(12) United States Patent
Kuroda et al.

(10) Patent No.: US 9,206,472 B2
(45) Date of Patent: Dec. 8, 2015

(54) METHOD FOR ANALYZING RNA

(75) Inventors: Toshihiko Kuroda, Kamakura (JP); Osamu Nomura, Kamakura (JP); Hitoshi Nobumasa, Kamakura (JP)

(73) Assignee: Toray Industries, Inc. (JP)

( * ) Notice: Subject to any disclaimer, the term of this patent is extended or adjusted under 35 U.S.C. 154(b) by 740 days.

(21) Appl. No.: 13/515,377

(22) PCT Filed: Dec. 15, 2010

(86) PCT No.: PCT/JP2010/072518
§ 371 (c)(1),
(2), (4) Date: Jun. 12, 2012

(87) PCT Pub. No.: WO2011/074592
PCT Pub. Date: Jun. 23, 2011

(65) Prior Publication Data
US 2012/0253687 A1  Oct. 4, 2012

(30) Foreign Application Priority Data

Dec. 16, 2009 (JP) .................. 2009-285098
Mar. 4, 2010 (JP) .................. 2010-047557
Oct. 26, 2010 (JP) .................. 2010-239513

(51) Int. Cl.
*G06F 19/20* (2011.01)
*C12Q 1/68* (2006.01)

(52) U.S. Cl.
CPC .............. *C12Q 1/6851* (2013.01); *G06F 19/20* (2013.01)

(58) Field of Classification Search
CPC ... A61K 2039/51; C12Q 1/6806; G01N 1/30; C12N 15/1003
See application file for complete search history.

(56) References Cited

FOREIGN PATENT DOCUMENTS

| JP | 2005-224172 A | 8/2005 |
| JP | 2008-035779 A | 2/2008 |
| JP | 2010-047557 | * 3/2010 |
| JP | 2010-239513 | * 10/2010 |
| WO | 2004/085681 A2 | 10/2004 |
| WO | 2004/090780 A2 | 10/2004 |
| WO | 2005/064019 A2 | 7/2005 |
| WO | 2006/119439 A2 | 11/2006 |
| WO | 2007/011902 A2 | 1/2007 |
| WO | 2008/021419 A2 | 2/2008 |
| WO | 2009/127350 | 10/2009 |
| WO | 2010/025447 | 3/2010 |

OTHER PUBLICATIONS

Auer, H. et al., "Chipping Away at the Chip Bias: RNA Degradation in Microarray Analysis," Nature Genetics, Dec. 2003, vol. 35, No. 4, pp. 292-293.
Norikazu Masuda et al., :Analysis of chemical modification of RNA from formalin-fixed samples and optimization of molecular biology applications for such samples, Nucleic Acids Research, vol. 27, No. 22, 1999, pp. 4436-4443.
Sandrine Imbeaud et al., "Towards standardization of RNA quality assessment using user-independent classifiers of microcapillary electrophoresis traces," Nucleic Acids Research, vol. 33, No. 6, 2005, pp. e56(1-12).
Andreas Schroeder et al., "The RIN: an RNA integrity number for assigning integrity values to RNA measurements," BMC Molecular Biology, vol. 7, No. 3, Jan. 31, 2006, pp. 1-14.
Kunihisa Nagino et al., "Ultrasensitive DNA Chip: Gene Expression Profile Analysis without RNA Amplification," The Journal of Biochemistry, vol. 139, No. 4, pp. 697-703.
Alfredo Ribeiro-Silva et al., "RNA extraction from ten year old formalin-fixed paraffin-embedded breast cancer samples: a comparison of column purification and magnetic bead-based technologies," BMC Molecular Biology, vol. 8, Dec. 21, 2007, pp. 118(1-10).
M. Jarzab et al., "Optimization of the Method of RNA Isolation from Paraffin Blocks to Assess Gene Expression in Breast Cancer," Polish Journal of Pathology, vol. 59, No. 2, 2008, pp. 85-91.
Fumiaki Sato et al., "Intra-Platform Repeatability and Inter-Platform Comparability of MicroRNA Microarray Technology," PLoS One, vol. 4, No. 5, May 2009, pp. e5540 (1-12).
Tatsuyuki Gorno et al., "mRNA Expression Analysis Extracted from Formalin-Fixed Paraffin-Embedded Samples," Bulletin of School of Health Sciences Tohoku University, vol. 18, No. 2, Jul. 31, 2009, pp. 101-110.
M. Mraz et al., "MicroRNA isolation and stability in stored RNA samples," Biochemical and Biophysical Research Communications, vol. 390, No. 1, Dec. 4, 2009, pp. 1-4.
Yu Shimada et al., "Paraffin Rinsho Kentai o Riyo shita mRNA to miRNA Kaiseki Yogo ya Yakuzai Kanjusei Yosoku Marker Idenshi Tansaku no Kanosei," Japanese Journal of Cancer Clinics, vol. 55, No. 8, Dec. 15, 2009, pp. 56-57 (partial translation).

* cited by examiner

*Primary Examiner* — John S Brusca
(74) *Attorney, Agent, or Firm* — DLA Piper LLP (US)

(57) ABSTRACT

A method of analyzing RNA extracted from a tissue or cell(s) fixed with a fixative, said method comprising a determining step of whether said RNA satisfies: B/A≤1 wherein A represents the weight ratio (%) of RNA within the range of 1000 to 4000 nucleotides with respect to the total weight of RNA as determined by electrophoresis; and B represents the weight ratio (%) of RNA within the range of more than 4000 nucleotides with respect to the total weight of RNA as determined by electrophoresis.

9 Claims, 2 Drawing Sheets

METHOD FOR ANALYZING RNA

RELATED APPLICATIONS

This is a §371 of International Application No. PCT/JP2010/072518, with an international filing date of Dec. 15, 2010 (WO 2011/074592 A1, published Jun. 23, 2011), which is based on Japanese Patent Application Nos. 2009-285098, filed Dec. 16, 2009, 2010-047557, filed Mar. 4, 2010, and 2010-239513, filed Oct. 26, 2010, the subject matter of which is incorporated by reference.

TECHNICAL FIELD

This disclosure relates to a method for analyzing RNA extracted from a tissue or cell(s) fixed with a fixative.

BACKGROUND

In recent years, development of techniques to analyze genes in a vast number of samples that are stored in hospitals and research institutes in the forms of tissues and cells fixed with a fixative, such as formalin-fixed paraffin-embedded (FFPE) tissues, has been increasingly demanded. Since, especially as FFPE tissues, a vast amount of data on diseases obtained in the past have been accumulated, establishment of a technique that enables extraction, and analysis of expression, of genes extracted from FFPE tissues allows retrospective studies using tissues stored for a long period, largely contributing to future therapy and prophylaxis of diseases.

However, since degradation and fragmentation of RNAs extracted from fixed tissues and fixed cells such as FFPE samples proceed under general fixation conditions and storage conditions, it has been thought that gene expression analysis is difficult with such RNA. Further, formaldehyde (formalin), which is most commonly employed as a fixative, sometimes causes RNA-RNA or RNA-protein cross-linking, or addition of formaldehyde to RNA or modification of RNA with formaldehyde. In cases where RNA is in such a state, enzymatic reactions and/or chemical reactions hardly proceed, resulting in difficulty in analyzing gene expression. Therefore, a technology has been demanded by which analysis of gene expression can be carried out with an RNA sample showing extensive degradation and/or fragmentation, or with an RNA sample wherein cross-linking, addition and/or modification occurred. Further, it is very useful to judge, before gene expression analysis of such an RNA sample, the quality of the RNA sample by confirmation of the degrees of degradation/fragmentation, cross-linking and addition/modification to confirm whether or not the analysis is possible, for performing an accurate gene expression analysis and miRNA expression analysis, and hence a technique that enables such judgment has been demanded.

Japanese Translated PCT Patent Application Laid-open No. 2006-520603, JP 2005-224172 A, Japanese Translated Patent Application Laid-open No. 2007-515964 and Japanese Translated PCT Patent Application Laid-open No. 2008-541699 disclose techniques related to methods wherein gene expression analysis is performed after amplification of degraded RNA.

JP '603 provides a method, composition and kit related to amplification of a target polynucleotide to produce a large number of its copies. The amplification factor of mRNA per each time of amplification reaction is normally 50 to 100 or up to 250; 500 to 1000; or 500 to not less than 2000; and as much amplified RNA as possible is obtained from total RNA in an amount of less than a nanogram. However, in cases where such a method wherein RNA is amplified as much as possible from a small amount of RNA is employed, the amplification factor varies among genes, that is, the amplification bias increases, so that it can be said that the expression level of each gene cannot be analyzed accurately.

JP '172 relates to a method for using fragmented RNA or the like such as that contained in a stored fixed paraffin-embedded tissue material in comprehensive gene expression profiling, and provides a method of preparation of a sample that enables comprehensive amplification even from a sample composed of very small or extremely fragmented RNA. However, that method comprises a step of polyadenylation of fragmented RNA and, as a result, variation of the reaction in this step may largely influence the gene expression profile. Further, JP '172 discloses a novel linear RNA amplification method. In that method, a double-stranded cDNA having an anchor sequence at the 5'-end and an RNA polymerase promoter sequence at the 3'-end is synthesized, and cRNA is synthesized from the cDNA dependently on the RNA polymerase promoter sequence, followed by priming the anchor sequence to synthesize cDNA again from this cRNA, thereby amplifying a small amount of RNA obtained from a small amount of cells/tissue obtained by laser capture microdissection or cell sorting, to suppress deletion of the region of cDNA and cRNA corresponding to the 5'-region of mRNA that occurs every time the cDNA synthesis-cRNA synthesis cycle is repeated, which has been problematic in known amplification methods.

The methods in both JP '603 and JP '172 are described as methods showing no amplification bias, and it is thought that the bias per each cycle is smaller than that in conventional methods. However, since they focus on amplification of as much RNA as possible from a small amount of RNA, the amplification factor is considerably large. Accordingly, the bias may accumulate, resulting in occurrence of a large amplification bias.

JP '964 relates to a method for using fragmented RNA or the like such as that contained in a stored fixed paraffin-embedded tissue material in comprehensive gene expression profiling, and provides a method of preparation of a sample that enables comprehensive amplification even from a sample composed of very small or extremely fragmented RNA. However, that method comprises a step of polyadenylation of fragmented RNA, and, as a result, variation of the reaction in this step may largely influence the gene expression profile.

JP '699 discloses a composition and a method for amplifying a target in a degraded nucleic acid sample including a method for measuring the quality of nucleic acid in the nucleic acid sample, and also discloses a method for preparing a gene expression profile using a degraded RNA sample. The amplification efficiencies of amplicons (amplification products) having different sizes derived from the same gene are used as indices for evaluation of the quality, in view of the fact that the amplification efficiency of an amplicon having a large size decreases as degradation of the sample proceeds. That method performs multiple size PCR about each of ten to twenty and several genes. In cases where degradation of RNA has proceeded, amplification becomes less likely to occur as the PCR probe size increases, so that it is considered that the degree of degradation can be confirmed to a certain degree. However, since PCR amplification of a total of several ten genes is required per one RNA sample, it is thought that that method is difficult to actually carry out.

JP 2008-35779 A discloses a method wherein degradation index nucleic acid probes designed based on the base sequences of RNAs that are contained in the long-chain fraction if those are not degraded are loaded on a nucleic acid array, and an RNA sample prepared by fractionation of short chains from total RNA is hybridized with the nucleic acid array, followed by measuring, based on the presence/absence of signals from the degradation index nucleic acid probes, the degree of degradation of the RNA sample; and a technique related to the nucleic acid array for measurement of the degree of degradation of RNA. However, since the nucleic acid array is specified to short chain RNAs such as microRNA (miRNA), it is thought that application of the array to gene expression analysis is difficult. Further, in cases where RNA is extracted from a fixed tissue or fixed cell(s) such as FFPE, the amount of RNA which can be obtained is often small unlike cases of extraction of RNA from a cell(s) or a frozen tissue, and, under such conditions, it is not realistic to carry out an experiment using a sample in an amount of as much as several to several ten micrograms just for confirmation of the quality of the RNA sample. Also in view of the cost, that method can never be said to be a preferred method.

In JP 2008-43332 A, there is a description on a method for measuring the fragmentation level of nucleic acid. It discloses a kit for judging whether or not analysis of an RNA sample is possible, which judgment is made by measuring the amounts of 2 kinds of ribosomal RNA (18S and 28S) to determine the 28S/18S ratio. It is said that, when RNA is degraded, 28S is first degraded, and 18S is subsequently degraded. In that kit, in cases where 28S/18S is not more than 0.1, RNA is judged to have a bad quality. However, in terms of RNA extracted from a tissue or cell(s) fixed with a fixative, the RNA is generally degraded during fixation, and more-over, since fixed tissues and cells are normally stored at room temperature, the RNA is further degraded with time. Therefore, the above-described 2 kinds of ribosomal RNA often cannot be detected in RNA extracted from a formalin-fixed paraffin-embedded (FFPE) tissue, and, in such cases, according to the above-described standard for judgment of the quality of an RNA sample, most samples are determined to be unanalyzable. Thus, it is very difficult to use the kit for carrying out a retrospective study using a fixed tissue or fixed cell(s) stored for a long period.

Japanese Translated PCT Patent Application Laid-open No. 2009-501531 is a method of profiling of RNA wherein miRNA in a stored tissue containing degraded mRNA, which miRNA is bound to RISC(RNA-induced silencing complex) and not degraded, is released by heat treatment or the like, followed by detection of the miRNA by PCR amplification. Since the release of miRNA from RISC requires treatment at a high temperature of 95° C., the possibility of occurrence of degradation in this process cannot be excluded, and it does not mention a method for confirming the quality of RNA.

Further, in cases where a capillary electrophoresis system (e.g., "Bioanalyzer" manufactured by Agilent Technologies) is employed, RIN (RNA Integrity Number), which is a measurement standard developed by Agilent Technologies, is calculated as an index of RNA degradation. RIN is calculated based on the entire electropherogram of the RNA sample subjected to electrophoresis, and varies within the range of 0 to 10 (A. Schroeder, O. Mueller, S. Stocker, R. Salowsky, M. Leiber, M. Gassmann, S. Lightfoot, W. Menzel, M. Granzow and T. Ragg, "The RIN: an RNA integrity number for assigning integrity values to RNA measurements," BMC Molecular Biology 7:3 (2006)). Bioanalyzer manufactured by Agilent Technologies is an apparatus commonly used for evaluation of the quality of nucleic acid and, in cases where this apparatus is employed, RIN is an index commonly used for representing the quality of RNA. However, when RNAs extracted from fixed tissues or fixed cells were analyzed with Bioanalyzer, even RNAs with clearly different electropherograms and various degradation behaviors show almost the same RIN values between 2 and 3. Therefore, there has been a possibility that RIN did not necessarily reflect the actual state of RNA. Means to judge whether or not RNA extracted from various tissues or cells fixed with a fixative can be subjected to the analysis is actually limited.

When RNA extracted from a tissue or cell(s) fixed with a fixative was to be analyzed, no method has been available to judge, simply and with a high probability, whether or not the extracted RNA is suitable for the analysis, and it was therefore difficult to know the appropriateness of data obtained by the analysis.

SUMMARY

We discovered that, when gene expression analysis of RNA extracted from a tissue or cell(s) fixed with a fixative is to be carried out, highly appropriate and reproducible data reflecting the original abundance of the RNA can be obtained by subjecting, before the analysis, the RNA to electrophoresis and judging whether or not the RNA is suitable for the analysis based on the pattern of electrophoresis, followed by carrying out the analysis in cases where the RNA was judged to be suitable for the analysis.

We further discovered that, in cases where the amplification factor for amplification of the RNA is set to 2 to 20 with respect to the original RNA amount, the bias due to amplification can be suppressed. Hence, highly appropriate and reproducible data reflecting the original abundance of the RNA can be obtained.

We thus provide:

(1) A method for analyzing RNA extracted from a tissue or cell(s) fixed with a fixative, the method comprising a step wherein whether the RNA satisfies the following equation:

$$B/A \leq 1 \qquad \text{Equation:}$$

wherein A represents the weight ratio (%) of RNA within the range of 1000 to 4000 nucleotides with respect to the total weight of RNA as determined by electrophoresis, and B represents the weight ratio (%) of RNA within the range of more than 4000 nucleotides with respect to the total weight of RNA as determined by electrophoresis.

(2) The method for analyzing RNA according to (1), the method further comprising a step wherein whether the ratio A (%) is not less than 25%.

(3) The method for analyzing RNA according to (1) or (2), wherein an amplification product obtained by amplification of the RNA with an amplification factor of 2 to 20 is analyzed.

(4) The method for analyzing RNA according to (1) or (2), wherein the RNA is analyzed without amplification.

(5) The method for analyzing RNA according to (4), wherein the RNA is miRNA.

(6) The method for analyzing RNA according to any of (1) to (5), wherein the fixative comprises formaldehyde and/or paraformaldehyde.

(7) The method for analyzing RNA according to any of (1) to (6), wherein the tissue or cell(s) fixed with a fixative is/are embedded in paraffin or embedded in OCT compound.

(8) A method of analyzing RNA including extracting the RNA from a fixed tissue or cell(s); and determining whether the RNA satisfies:

$$B/A \leq 1$$

wherein A represents the weight ratio (%) of RNA within the range of 1000 to 4000 nucleotides with respect to the total weight of RNA as determined by electrophoresis, and B represents the weight ratio (%) of RNA within the range of more than 4000 nucleotides with respect to the total weight of RNA as determined by electrophoresis.

(9) A method of analyzing RNA extracted from a tissue or cell(s) fixed with a fixative including measuring weight of RNA comprising 1000 to 4000 nucleotides from the extracted RNA by electrophoresis; measuring weight of RNA comprising more than 4000 nucleotides from the extracted RNA by electrophoresis; and determining whether the RNA satisfies: B/A≤1, wherein A represents a weight ratio (%) of the RNA comprising 1000 to 4000 nucleotides with respect to total weight of the extracted RNA, and B represents a weight ratio (%) of the RNA comprising more than 4000 nucleotides with respect to the total weight of the extracted RNA.

By the method for analyzing RNA, analysis accurately reflecting the original abundance of a gene is possible even with RNA extracted from a tissue or cell(s) fixed with a fixative, and a preferred effect can be obtained especially in microarray analysis. Further, by our method for analyzing RNA, whether or not RNA extracted from a tissue or cell(s) fixed with a fixative is suitable for analysis can be judged before the analysis, and waste of reagents and the like can therefore be prevented in advance.

DETAILED DESCRIPTION

Figure 1:
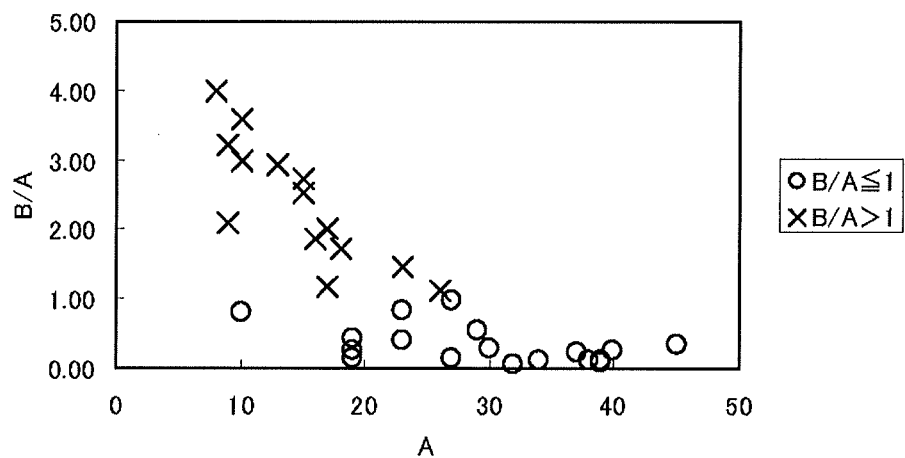
FIG. 1 shows a diagram prepared by defining the weight ratio (%) of RNA within the range of 1000 to 4000 nucleotides as A and the weight ratio (%) of RNA within the range of more than 4000 nucleotides as B, which ratios were determined for various RNAs using Bioanalyzer, and plotting A along the abscissa and B/A along the ordinate.

"Tissue or cell(s) fixed with a fixative" means a tissue or cell(s) subjected to a treatment for maintaining a biological sample in a state as natural as possible by immersing a tissue or cell(s) in a solution called a fixative, that is, fixation treatment. Preferred examples of the fixative used in this treatment include formaldehyde solutions; paraformaldehyde solutions; solutions containing an alcohol such as ethanol or methanol, acetone or chloroform; fixatives containing an acid such as picric acid or potassium dichromate (e.g., Bouin's fixative, Zamboni's fixative or Orth's fixative); and solutions containing a metal such as zinc acetate, zinc chloride or zinc sulfate. Further, mixtures of 2 or more kinds of the above solutions, such as Carnoy's fixative, which is composed of ethanol, chloroform and acetic acid; and methacam fixative, which is composed of methanol, chloroform and acetic acid; are also preferably used.

A solution containing formaldehyde or paraformaldehyde is more preferably used as the fixative. The formaldehyde solution may be prepared by diluting commercially available formalin (formaldehyde concentration, 37%) with water, or may also be preferably prepared by adjusting the pH of an aqueous solution to neutral with calcium carbonate, magnesium carbonate or the like, or by diluting formaldehyde with phosphate buffer to adjust the pH to neutral. Further, a formalin solution after removal of its bad odor and irritating odor and adjustment of its concentration (trade name: Maskedform) may be used. The formaldehyde content in the formaldehyde solution is preferably 1 to 30%, more preferably 2 to 20%. The paraformaldehyde solution may be prepared by dissolving paraformaldehyde powder in water, phosphate buffer or the like, or by dissolving paraformaldehyde powder in water and a small amount of sodium hydroxide and then adjusting the pH with phosphate buffer or the like to neutral; or a commercially available paraformaldehyde solution may be used. The concentration is preferably 1 to 10%, more preferably 2 to 8%.

The fixed tissue or cell(s) may be embedded in paraffin. In cases where the fixed tissue or cell(s) is/are embedded in paraffin, the operation may be carried out according to a commonly used technique known to those in the art. That is, a fixed tissue or cell(s) is/are subjected to substitution with alcohol to dehydrate the tissue or cell(s), followed by substitution with xylene, benzene or the like. Thereafter, in a mold into which paraffin melt by heating was poured, the tissue or cell(s) is/are placed and embedded, to provide a paraffin block. When RNA is extracted from the paraffin-embedded tissue or cell(s), the tissue or cell(s) is/are sliced using a microtome such as a rotary microtome or sliding microtome before use. The thickness of each thin section is not restricted, and preferably 1 to 100 μm, more preferably 2 to 50 μm. Alternatively, instead of paraffin, OCT (Optimal Cutting Temperature) compound, which is mainly used for preparation of frozen tissue sections, may be used. A method by extraction of RNA from a tissue recovered by microdissection or the like is also preferably employed, wherein a paraffin block is sliced and attached to a slide glass, and a part thereof is collected by laser-capture microdissection (LCM), use of a scalpel, or the like to collect a tissue to be analyzed. In cases where LCM is carried out, tissue or cell(s) may be stained to increase their visibility for secure recovery of the tissue or cell(s) to be analyzed. As the dye to be used in this treatment, cresyl violet, hematoxylin-eosin (HE), nuclear fast red (NFR) or the like may be used.

"RNA extracted from a tissue or cell(s) fixed with a fixative" is RNA extracted from a tissue or cell(s) fixed using the above-mentioned fixative, by digesting proteins in the tissue or cell(s) with an enzyme. Examples thereof include mRNA, rRNA, tRNA and miRNA, and the RNA is preferably mRNA or miRNA, more preferably miRNA. Since the extract may be contaminated with impurities such as DNA and proteins, an operation of purification is preferably carried out after the extraction. The method of purification used in this operation is not restricted, and examples thereof include a method wherein a column having a silica membrane, anion-exchange resin or the like is used, a method wherein liquid chromatography such as reversed-phase chromatography is used, a method wherein RNA is precipitated using an organic solvent, a method wherein an ammonium acetate solution at a high concentration is added to a solution containing RNA to selectively precipitate the RNA, and a method wherein magnetic beads are used. In the above-mentioned extraction and purification, an RNA extraction kit for formalin-fixed paraffin-embedded tissues, such as "RecoverAll (trademark) Total Nucleic Acid Isolation Kit for FFPE" (Ambion), "RNeasy FFPE Kit" (Qiagen), "ISOGEN PB Kit" (Nippon Gene Co., Ltd.), "FFPE RNA Purification Kit" (Norgen), "PureLink (trademark) FFPE RNA Isolation Kit" (Invitrogen), "High Pure FFPE RNA Micro" (Roche Applied Science), "Agencourt FormaPure (trademark) Kit" (Beckman Coulter) or "QuickExtract (trademark) FFPE Extraction Kit" (Epicentre) may be preferably used.

Since components of the fixative may cause degradation and/or cross-linking/modification of RNA extracted from a tissue or cell(s) fixed with the above-described fixative, it has been difficult, in many cases, to subject the sample to analysis utilizing an intermolecular interaction with a substance which can directly or indirectly, and selectively bind to the RNA (hereinafter referred to as a selective binding substance). Therefore, judgment in advance of whether or not the sample is suitable for the analysis has been a technical problem. As described in the later-mentioned Examples and the like, we discovered that whether or not RNA extracted from a fixed tissue or cell(s) is suitable for the microarray analysis can be judged by carrying out the step of confirmation of the weight ratio of RNA within the range of 1000 to 4000 nucleotides with respect to the total weight of RNA as determined by electrophoresis and the weight ratio of RNA within the range of more than 4000 nucleotides with respect to the total weight of RNA as determined by electrophoresis, to preliminarily eliminate RNA samples containing high ratios of low-molecular-weight RNA as an index of degradation and fragmentation of RNA and/or high-molecular-weight RNA as an index of cross-linking and addition/modification of RNA.

"Suitable for analysis" herein means a state where, when RNA was analyzed utilizing an intermolecular interaction between the RNA and a selective binding substance, information retained by the sample can be accurately measured. As described above, when RNA is subjected to analysis, in cases where the degrees of degradation and fragmentation are high or a large amount of products due to cross-linking or addition/modification exist, the intermolecular interaction with a selective binding substance may be inhibited, amplification may not produce a sufficient amount of product, or a bias may occur, so that it is highly possible that accurate analysis cannot be done.

In terms of RNA extracted from a fixed tissue or cell(s), examples of the method of confirmation of the weight ratio of RNA within the range of 1000 to 4000 nucleotides with respect to the total weight of RNA as determined by electrophoresis and the weight ratio of RNA within the range of more than 4000 nucleotides with respect to the total weight of RNA as determined by electrophoresis include a method wherein the RNA is sorted based on the molecular weight and quantifying the abundance ratio of RNA within each molecular weight range. Particular examples of electrophoresis as a means to sort an RNA sample extracted from a fixed tissue, cell(s) or the like based on the molecular weight to confirm the molecular weight distribution include agarose gel electrophoresis, polyacrylamide gel electrophoresis, capillary electrophoresis and chip electrophoresis. Examples of the means to quantify the abundance ratio of RNA within a particular nucleotide range include, in the cases of gel electrophoresis, methods wherein various densitometers or imagers such as "Typhoon" (GE Healthcare) known to those in the art are used to digitize the band intensity. In cases where chip electrophoresis is carried out using an electrophoresis system such as "Agilent 2100 Bioanalyzer" (Agilent Technologies), the abundance ratio of RNA within a particular molecular weight range can be suitably calculated by performing Smear analysis included in the dedicated software. It should be noted that, in cases where undegraded RNA (intact RNA) is analyzed by electrophoresis, 28S ribosomal RNA, which is said to have about 4700 nucleotides may appear as a band having a peak at a molecular weight corresponding to that of RNA having a little less than 4000 nucleotides. It is thought that this is due to the fact that each 28S molecule contains many double-stranded regions and, hence, has a compact structure resulting in a migration rate faster than expected from its actual molecular weight. A similar description on this phenomenon can be found in FAQ shown in the home-page of Agilent Technologies. Therefore, we regard 28S ribosomal RNA as being substantially within the range of 1000 to 4000 nucleotides in electrophoresis. Further, since the molecular weight of 18S corresponds to that of 1874 nucleotides and the band of 18S appears within the range of 1000 to 4000 nucleotides in electrophoresis, 18S is of course included within the range.

The particular method for judging whether or not RNA extracted from a fixed tissue or cell(s) is/are suitable for the analysis is a method wherein whether or not A, the weight ratio (%) of RNA within the range of 1000 to 4000 nucleotides with respect to the total weight of RNA as determined by electrophoresis, is smaller than or the same with B, the weight ratio (%) of RNA within the range of more than 4000 nucleotides with respect to the total weight of RNA as determined by electrophoresis, is confirmed, that is, whether or not $B/A \leq 1$ is satisfied is confirmed, to judge whether or not the sample can be suitably subjected to the analysis. We believe that the fraction containing RNA longer than 4000 nucleotides contains cross-linked RNA, which may be incapable of hybridizing with a probe. Therefore, in cases where an RNA sample wherein the ratio B is larger than the ratio A is analyzed, the quantified value tends to be smaller than the amount of actually existing mRNA or miRNA, and there is even a case where mRNA or miRNA cannot be detected even if it is essentially expressed. Thus, before carrying out analysis of RNA extracted from a fixed tissue or cell(s), by confirming whether or not B/A of the RNA is not more than 1, whether or not the RNA is suitable for the analysis can be promptly judged.

In the case of RNA corresponding to $B/A \leq 1$, a high correlation can be obtained with results of microarray analysis of undegraded (intact) RNA extracted from the same tissue or cell(s). The correlation coefficient herein means an index quantitatively representing the strength of correlation between 2 data and varies between −1 and 1. A positive value represents a positive correlation; a negative value represents a negative correlation, and the value zero represents no correlation. In general, in cases where the absolute value is not less than 0.5, it can be judged that there is a correlation; in cases where the absolute value is less than 0.5, it can be judged that there is no correlation; and the stronger the degree of correlation between 2 data, the closer the absolute value to 1. For calculation of the correlation coefficient with "Microsoft Office Excel" (Microsoft), the function "correl" may be used. When the correlation coefficient was determined for genes whose expression was found in common between the two samples, the value is preferably not less than 0.7, more preferably not less than 0.8, still more preferably not less than 0.9.

Further, in RNA extracted from a fixed tissue or cell(s), the higher A, the weight ratio (%) of RNA within the range of 1000 to 4000 nucleotides with respect to the total weight of RNA as determined by electrophoresis, the closer the RNA to the intact state having no degradation, in which case there is a greater tendency to obtain expression behaviors of genes or miRNAs similar to those of intact RNA. More particularly, whether or not the RNA is in a state close to the intact state can be more promptly judged in cases where the ratio A is preferably not less than 15%, more preferably not less than 20%, still more preferably not less than 25%.

Further, a smaller value of (A+B), which is the sum of A, the weight ratio (%) of RNA within the range of 1000 to 4000 nucleotides with respect to the total weight of RNA as determined by electrophoresis, and B, the weight ratio (%) of RNA within the range of more than 4000 nucleotides with respect to the total weight of RNA as determined by electrophoresis (0≤(A+B)≤100), indicates a higher weight ratio of RNA smaller than 1000 nucleotides, that is, a larger amount of degraded RNA. In cases where the amount of degraded RNA is large, the possibility of occurrence of a phenomenon called cross hybridization, wherein RNA other than the RNA whose hybridization is originally expected is bound to the probe, may be high especially in cases where microarray analysis of short-chain miRNA is to be carried out. In such cases, the obtained result may suggest stronger expression of RNA than expected from the actual abundance of the RNA, or may suggest a larger number of expressed RNA than the actual number thereof. The value of A+B is preferably (A+B)≥15, more preferably (A+B)≥20, still more preferably (A+B)≥25.

Further, it is also preferred to detect the presence/absence of a particular gene in RNA extracted from a fixed tissue or cell(s), to judge, in more detail, whether or not the RNA can be analyzed. By performing this operation, whether or not the analysis is possible may be judged at a higher rate. In such a case, cDNA is synthesized by reverse transcription of RNA, and the cDNA is used as a template to amplify a particular gene by PCR. The resulting amplification product is then evaluated by electrophoresis, and in cases where the presence of the particular gene could be recognized, the RNA is judged to be analyzable. As the particular gene herein, a gene which is considered to theoretically hardly show variation among samples, such as one called a housekeeping gene or internal control is preferably selected. Examples of the gene include glyceraldehyde-3-phosphate dehydrogenase, β-actin, β2-microglobulin, hypoxanthine ribosyltransferase, porphobilinogen deaminase, phosphoglycerate kinase, cyclophilin A and β-glucuronidase.

Our methods are not restricted as long as the analysis utilizes an intermolecular interaction between RNA and a selective binding substance, and preferred examples of the analysis tool include microarrays.

A microarray is prepared by immobilizing a plurality of types of selective binding substances on a substrate composed of an inorganic material(s) such as glass, ceramics and/or silicone; metal(s) such as stainless steel and/or gold (gilding); and/or macromolecular material(s) such as polyethylene terephthalate, polymethylmethacrylate (PMMA), cellulose acetate, polycarbonate, polystyrene, polydimethylsiloxane and/or silicone rubber; and useful as an analysis tool for detecting the presence/absence of binding between the immobilized plurality of types of selective binding substances and a test substance, and the levels of binding of the test substance, at once. Examples of the selective binding substances immobilized on the microarray include nucleic acids and other antigenic compounds. Examples of the nucleic acids include deoxyribonucleic acid (DNA), ribonucleic acid (RNA), peptide nucleic acid (PNA), complementary DNA (cDNA) and complementary RNA (cRNA). Examples of the other antigenic compounds include low-molecular-weight compounds. An especially preferred selective binding substance is a nucleic acid. Such a selective binding substance may be one commercially available, may be synthesized, or may be prepared from a natural source such as a biological tissue or cells.

The microarray is not restricted, and preferred examples thereof include ones having an irregular portion(s) on the surface of the substrate, wherein a cover may further be provided on the top of a protruded portion(s). In such a case, the cover preferably has one or more penetrating holes communicating with a void(s). These holes are for injection of a liquid(s) such as a nucleic acid solution and/or a buffer for binding, and, at the same time, for maintaining the pressure inside the substrate at the atmospheric pressure. There are preferably a plurality of the penetrating holes per one void, and the number of holes is especially preferably 3 to 6 in view of simplicity of filling with a sample solution. The method of production of the above-described cover is not restricted, and preferred examples of the method include injection molding, hot embossing and machining in the case of a resin; sandblasting in the case of glass or ceramics; and methods used in known semiconductor processes in the case of silicone. Further, by encapsulating microparticles between the microarray and the cover, it is possible, after applying a sample solution to the void(s), to apply vibration to the sample solution to make the encapsulated microparticles move vigorously in the solution. As a result, the stirring efficiency remarkably increases, and an effect of promoting the hybridization reaction is exerted, which is preferred. The material of the microparticles herein is not restricted, and preferred examples of the material include glass, ceramics (e.g., yttria-stabilized zirconia), metals (e.g., stainless steel), polymers (e.g., nylons and polystyrenes) and magnetic bodies. Among these, ceramic microparticles are preferably employed since these are physically and chemically stable and have a large specific gravity. By further using a method wherein the substrate is rotated to make the microparticles fall to the direction of gravity, a method wherein the substrate is shaken, a method wherein magnetic microparticles are used and the microparticles are moved by application of the magnetic force, or the like in combination, the stirring efficiency can be further enhanced.

The RNA extracted from a tissue or cell(s) fixed with a fixative (hereinafter also referred to as a test substance) may be subjected to analysis without amplification (product without amplification), or an amplification product of the RNA may be subjected to analysis. The process is appropriately selected depending on the type of the test substance. For example, in cases where miRNA is to be analyzed, analysis without amplification is preferred. In cases where mRNA is to be analyzed, the test substance may be either a product without amplification or an amplification product, but in cases where a test substance requiring prevention of an amplification bias is to be analyzed, a product without amplification, or an amplification product prepared by amplification with an amplification factor of 2 to 20 as mentioned below is preferably analyzed.

In cases where an amplification product is to be analyzed, the method of amplification of RNA is not restricted, and amplification kits commercially available from various companies, which are applicable to FFPE may be used. In cases where a commercially available kit is used, preferred examples of the kit include "ExpressArt FFPE RNA Amplification Kit" (AmpTec), "WT-Ovation FFPE System V2" (NuGen) and "Arcturus Paradise Plus Reagent System" (MDS Analytical Technologies). Further, it is also preferred to use "SenseAMP Plus", "RumpUp" or "RumpUp Plus" (Genisphere) for synthesizing sense-strand RNA, followed by synthesizing antisense-strand RNA by a known method.

Further, as mentioned above, an amplification product prepared by amplification with an amplification factor of 2 to 20 is preferably analyzed. It is thought that in cases where the amplification factor is only less than 2 when an amplification product is obtained from RNA, the RNA shows extensive degradation and fragmentation and is composed of very short RNA chains, or the amplification reaction is inhibited by cross-linking occurred between RNA molecules or between RNA and protein or by addition/modification due to binding of a fixative-derived substance such as formaldehyde to RNA during fixation, leading to the absence of amplification or insufficient amplification reaction. As a result, accurate analysis may be impossible. Further, in cases where an amplification product is obtained with an amplification factor of more than 20, there may be a high possibility that a remarkable amplification bias appears, wherein, for example, RNA less influenced by degradation or the like is more likely to be amplified, while RNA with considerable degradation is hardly amplified.

The amplification product may be either DNA obtained by RT-PCR or the like or RNA synthesized by RNA polymerase or the like, and the amplification product is preferably RNA. Further, in cases where the amplification product is RNA, the RNA is not restricted and may be either sense-strand RNA or antisense-strand RNA. Since most of existing microarrays have probes applicable to anti-sense strand RNA, the RNA is preferably amplified into antisense-strand RNA in cases where an existing microarray is used.

Examples of the method for achieving an amplification factor of 2 to 20 include a method wherein the concentrations of the enzyme, primer, substrate and/or the like used for the amplification of RNA is increased and/or decreased to optimize the composition of the reagent. Further, there is also a method by adjustment of the reaction time to achieve an amplification factor of 2 to 20. For example, in cases where an RNA sample extracted from a tissue or cell(s) is amplified using a reagent which yields a relatively high amplification factor, the reaction time is preferably shorter than the predetermined time. The number of times of amplification is preferably one. In cases where the amplification reaction is repeated 2 or more times, occurrence of even a small bias of the amplification product due to the first amplification may result in sharp increase in the bias in the second or later amplification. To determine the RNA weight in the solution in this step, for example, spectrophotometric measurement is performed for the RNA solution using a cell having an optical path length of 10 mm at a wavelength of 260 nm, and, based on the obtained value and the solution volume, calculation is carried out according to Equation A below:

(value at 260 nm)×40 (ng/μL)×solution volume (μL).  Equation A:

For confirmation of whether or not the amplification factor as a result of amplification of RNA is 2 to 20, the RNA weight in the solution after the amplification may be calculated according to the above Equation A based on the measurement value obtained with a spectrophotometer using a cell having an optical path length of 10 mm at a wavelength of 260 nm and the solution volume, followed by calculating the amplification factor according to Equation B below:

(RNA weight after amplification)/(RNA weight before amplification).  Equation B:

The test substance is preferably labeled with a known substance for labeling nucleic acid, and more preferably fluorescently labeled. In cases where the test substance is fluorescently labeled, fluorescent labeling may be carried out either before or after binding of the test substance to a selective binding substance. In cases where the test substance is a product without amplification, the substance is preferably directly labeled, and examples of the reagent for direct labeling to be used herein include "PlatinumBright Nucleic Acid Labeling Kit" (Kreatech; The fluorescent dyes are Dyomics series (Dyomics)), "ULS (trademark) microRNA Labeling Kit" (Kreatech; The fluorescent dyes are Cy3 and Cy5), "miRCURY LNA (trademark) miRNA Power Labeling Kit" (Exiqon; The fluorescent dyes are Hy3 and Hy5) and "Flash-Tag RNA Labeling Kit" (Genesphere; The fluorescent dyes are Oyster-550 and Oyster-650). On the other hand, in cases where an amplification product is analyzed, aminoallyl, biotin or the like may be attached to a part of the nucleotide triphosphates (NTPs) (adenosine triphosphate (ATP), guanosine triphosphate (GTP), cytidine triphosphate (CTP) and uridine triphosphate (UTP)), for example, a part of UTP, which is employed for the amplification reaction, and the resultant may be used to introduce the reactive group such as aminoallyl or biotin to the amplification product, which is preferred since the amplified product can be simply fluorescently labeled. In cases where aminoallyl was introduced, coupling reaction easily occurs with a fluorescent dye having N-hydroxysuccinimide (NHS) at its terminus. Examples of the fluorescent dye used herein include Cy3, Cy5 and Hyper 5 (GE Healthcare) and "Alexa Fluor" (registered trademark) series (Molecular Probes). Alternatively, without introduction of a reactive group such as aminoallyl, a reagent for direct fluorescent labeling of the amplified RNA may be used in the same manner as in the case of a product without amplification and, in such a case, the above-described reagents for direct labeling may be preferably used.

The fluorescently labeled test substance is subjected to binding reaction with selective binding substances immobilized on a carrier such as a microarray. As the method for binding the test substance to selective binding substances immobilized on a carrier, a known method is employed and, especially in cases where the selective binding substances are nucleic acids, a hybridization known method may be employed for the binding. Further, a known composition may be employed for the reaction solution used to bind the nucleic acid to the selective binding substances and, especially in cases where the selective binding substances are nucleic acids, a known hybridization buffer known to those in the art may be used. In terms of the method for detecting whether or not each selective binding substance immobilized on a carrier is bound to the test substance and for detecting the mass of the bound test substance, the detection/measurement can be performed using a known fluorescence scanning apparatus to read the intensity of fluorescence from the substance with which the nucleic acid is labeled.

EXAMPLES

Our methods will now be described in more detail by way of Reference Examples and Examples below. However, they are not restricted to the Examples below.

Reference Example 1

Confirmation of Yield of RNA in Operation of Fluorescent Labeling

In cases where microarray analysis is carried out using "3D-Gene (registered trademark) Human 25 k chip" (Toray Industries, Inc.), 1 μg of fluorescently labeled antisense RNA (aRNA) can be preferably prepared. Thus, conditions under which not less than 1 μg of fluorescently labeled aRNA can be obtained were studied. First strand cDNA was synthesized from RNA extracted from a frozen human gastric tissue, using reverse transcriptase ("SuperScript (registered trademark) III" (Invitrogen)), and DNA polymerase was then added thereto to synthesize the second strand cDNA, which is complementary to the first strand DNA. After purification of the synthesized cDNA using a silica-based column, in vitro transcription (IVT) using T7 RNA polymerase was performed at 42° C. for 8 hours, to allow amplification reaction of aRNA to proceed. This reaction was carried out 5 times to synthesize a total of 50 μg of aRNA. It should be noted that UTP to which an aminoallyl group (AA) was attached (AA-UTP) was included in the NTP mixture (ATP, GTP, CTP and UTP) used in the IVT reaction, to allow introduction of the AA group during the synthesis of aRNA. The operation of labeling of 1 μg, 2 μg, 3 μg or 4 μg of the synthesized AA-aRNA with Cy5 (GE Healthcare) was carried out 3 times, respectively. The amount of recovery of each sample after the labeling is shown in Table 1. It was shown that, 1 μg of fluorescently labeled aRNA for comprehensive gene analysis using a microarray can be obtained from not less than 2 μg of unlabeled amplified aRNA.

TABLE 1

| Amount of AA-aRNA before labeling (μg) | | 1.0 | 2.0 | 3.0 | 4.0 |
|---|---|---|---|---|---|
| Yield of labeled aRNA (μg) | First labeling | 0.5 | 1.2 | 1.9 | 2.7 |
| | Second labeling | 0.5 | 1.1 | 2.1 | 2.7 |
| | Third labeling | 0.4 | 1.2 | 2.0 | 2.9 |

Example 1

Extraction of RNA from Fixed Tissue

From each of 32 specimens obtained from FFPE samples of human gastric tissues, thin sections having a thickness of 10 μm were collected, and the sections were placed in a 1.5-mL tube. To this tube, 1 mL of xylene was added, and the resulting mixture was stirred to dissolve paraffin. After centrifugation at 16,000×g for 5 minutes, xylene was removed using a pipette such that the tissue was not sucked. Subsequently, 1 mL of ethanol was added to the tube, and the resulting mixture was stirred, followed by centrifuging the mixture at 16,000×g for 2 minutes and sufficiently removing ethanol such that the tissue was not sucked. This operation was carried out twice. The tube was dried in the air with its lid open for 10 minutes, to remove ethanol contained in the tissue. After addition of 100 μL, of a proteinase K solution (500 μg/mL), the tissue was suspended, and then left to stand at 37° C. for 16 hours. The tube was centrifuged at 16,000×g for 2 minutes to remove the residue, and RNA was then purified using a silica column. Tables 2 and 3 show the yield and the purity (ratio between 260 nm and 280 nm) measured using a spectrophotometer (Thermo Scientific, "Nano Drop" (registered trademark)); the weight ratio (%) of RNA within the range of 1000 to 4000 nucleotides, A, and the weight ratio (%) of RNA within the range of more than 4000 nucleotides, B, as calculated with "Agilent 2100 Bioanalyzer" (Agilent Technologies) (hereinafter referred to as Bioanalyzer); and B/A determined from the values A and B for each sample. FIG. 1 shows a diagram prepared by plotting A along the abscissa and plotting B/A along the ordinate, wherein each sample satisfying B/A≤1 is represented as "○" and each sample satisfying B/A>1 is represented as "x".

Amplification of RNA

From 1 μg each of the 18 samples satisfying B/A≤1, first strand cDNA was synthesized using reverse transcriptase ("SuperScript (registered trademark) III" (Invitrogen)), and DNA polymerase was then added thereto to synthesize the second strand cDNA, which is complementary to the first strand DNA. After purification of the synthesized cDNA using a silica-based column, in vitro transcription (IVT) using T7 RNA polymerase was performed at 42° C. for 8 hours, to allow amplification reaction of aRNA to proceed. In this reaction, AA-UTP was used to introduce aminoallyl groups during the amplification of aRNA, in the same manner as in Reference Example 1. The amplified aRNA was purified using a silica-based column. As shown in Table 2, the amplification factor calculated based on the yield after the amplification was not less than 2 in all the samples, and it was revealed that a sample satisfying B/A≤1 is suitable for the method for analyzing RNA.

Fluorescent Labeling and Fragmentation of Amplified RNA

The solution of each amplified aRNA was concentrated using a centrifugal concentrator (Tomy Seiko Co., Ltd.; MV-100) to about 1 μL. To the resulting concentrate, 5 μL of Sodium Bicarbonate Buffer, which is attached to the "3D-Gene (registered trademark) Hybridization Buffer" kit (Toray Industries, Inc.), was added, and the resulting mixture was stirred by pipetting, followed by adding 5 μL of Cy5-NHS (GE Healthcare) dissolved in DMSO thereto, stirring the resulting mixture by pipetting, and incubating the mixture at 40° C. for 1 hour to perform coupling reaction. Using a gel filtration spin column (BioRad), unreacted Cy5 was removed to purify each reaction solution, and nuclease-free water was added to the purified solution to attain a final volume of 32 μL. To the resulting solution, 8 μL of "5× Fragmentation Buffer", which is attached to the "3D-Gene (registered trademark) Hybridization Buffer" (Toray Industries, Inc.) kit, was added, and the resulting mixture was lightly stirred by pipetting, followed by treatment at 94° C. for 15 minutes. Each sample was rapidly cooled on crushed ice for 3 minutes and purified with "Microcon YM-10" (Millipore).

Hybridization

For each of the 18 samples satisfying B/A≤1, the labeled and purified aRNA was subjected to microarray analysis by the following operation. A solution containing 1000 ng of each RNA was prepared with nuclease-free water to a final volume of 16 μL, and 2 μL of "Hybridization Buffer A" in "3D-Gene" (registered trademark) Hybridization Buffer (Toray Industries, Inc.) was added thereto, followed by heat treatment of the resulting mixture at 95° C. for 5 minutes. The mixture was rapidly cooled on crushed ice for 3 minutes, and 232 μL of "Hybridization Buffer B" was added thereto, followed by stirring the resulting mixture by gentle pipetting, thereby preparing 250 μL of a sample solution. The sample solution was degassed under reduced pressure, and 210 μL of the solution was applied to "3D-Gene (registered trademark) entire mouse genomic DNA chip" (Toray Industries, Inc.). The holes at 4 positions on the cover were closed by sealing, and the chip was placed in a hybridization chamber (Takara Bio Inc., TX711) immobilized on the top panel of Bioshaker (Tokyo Rikakikai, MMS-210). The temperature in the chamber was set to 37° C., and the samples were stirred with swiveling rotation at 250 rpm, to allow the reaction to proceed for 16 hours.

Measurement of Fluorescence Signal Values

After washing the chip after the reaction, fluorescence signal values were measured with a scanner ("3D-Gene (registered trademark) Scanner" (Toray Industries, Inc.)), to count the number of effective spots. As a result, as shown in Table 2, the number of effective spots was uniformly large. Further, the same experiment was carried out with RNA extracted from frozen samples of the same tissue, and the correlation coefficient was calculated for the effective spots shared with each FFPE sample-derived RNA. The correlation coefficient herein is an index quantitatively representing the strength of the interrelationship between two data, and varies within the range between −1 and 1, wherein a positive value represents a positive correlation; a negative value represents a negative correlation, and the value zero represents no correlation. In general, in cases where the absolute value is not less than 0.5, it can be judged that there is a correlation; in cases where the absolute value is less than 0.5, it can be judged that there is no correlation; and the stronger the degree of correlation between two data, the closer the absolute value to 1. For calculation of the correlation coefficient with "Microsoft Office Excel" (Microsoft), the function "correl" may be used, which software was used also in the present Example. The correlation coefficient for each sample was as shown in Table 2, and high positive correlation with the frozen tissue-derived RNA was confirmed for all the samples.

Comparative Example 1

From 1 μg each of the 14 samples satisfying B/A>1, aminoallyl-modified aRNA (AA-aRNA) was amplified in the same manner as described above. The amplification factor calculated from the yield after the amplification was less than 2 in most samples as shown in Table 3, indicating insufficient labeling of the RNA. That is, it was revealed that, with a high probability, a sample satisfying B/A>1 is difficult to be subjected to analysis of RNA.

TABLE 2

(a)

| Tissue | Human gastric tissue FFPE | | | | | | | | | |
|---|---|---|---|---|---|---|---|---|---|---|
| | (1) | (2) | (3) | (4) | (5) | (6) | (7) | (8) | (9) | (10) |
| Purity (OD260/OD280) | 1.93 | 1.93 | 1.99 | 2.01 | 2.04 | 1.95 | 1.81 | 1.89 | 2.00 | 1.97 |
| Ratio of 1000-4000 [nt], A (%) | 27 | 23 | 29 | 27 | 37 | 23 | 19 | 20 | 45 | 30 |
| Ratio of more than 4000 [nt], B (%) | 26 | 19 | 16 | 4 | 8 | 9 | 3 | 16 | 15 | 9 |
| B/A | 0.96 | 0.83 | 0.55 | 0.15 | 0.22 | 0.39 | 0.16 | 0.80 | 0.33 | 0.30 |
| Amplification factor | 8.1 | 2.1 | 3.7 | 5.5 | 5.0 | 3.2 | 5.8 | 3.5 | 4.3 | 4.6 |
| Number of detected genes | 15480 | 13391 | 14423 | 16079 | 15549 | 14970 | 15989 | 14439 | 14777 | 15010 |
| Correlation coefficient | 0.95 | 0.88 | 0.91 | 0.92 | 0.92 | 0.90 | 0.94 | 0.90 | 0.95 | 0.93 |

(b)

| Tissue | Human gastric tissue FFPE | | | | | | | |
|---|---|---|---|---|---|---|---|---|
| | (11) | (12) | (13) | (14) | (15) | (16) | (17) | (18) |
| Purity (OD260/OD280) | 1.97 | 2.00 | 1.99 | 1.95 | 1.98 | 1.94 | 1.99 | 1.95 |
| Ratio of 1000-4000 [nt], A (%) | 39 | 39 | 34 | 40 | 32 | 38 | 19 | 19 |
| Ratio of more than 4000 [nt], B (%) | 3 | 4 | 4 | 10 | 2 | 4 | 5 | 8 |
| B/A | 0.08 | 0.10 | 0.12 | 0.25 | 0.06 | 0.11 | 0.26 | 0.42 |
| Amplification factor | 4.6 | 5.2 | 6.6 | 5.5 | 6.6 | 6.7 | 2.7 | 2.1 |
| Number of detected genes | 16801 | 17209 | 17560 | 17090 | 16778 | 17236 | 13809 | 13294 |
| Correlation coefficient | 0.95 | 0.94 | 0.93 | 0.96 | 0.90 | 0.91 | 0.90 | 0.88 |

TABLE 3

(c)

| Tissue | Human gastric tissue FFPE | | | | | | | | | |
|---|---|---|---|---|---|---|---|---|---|---|
| | (19) | (20) | (21) | (22) | (23) | (24) | (25) | (26) | (27) | (28) |
| Purity (OD260/OD280) | 1.91 | 1.93 | 1.90 | 1.97 | 1.89 | 1.93 | 1.86 | 1.95 | 1.90 | 1.95 |
| Ratio of 1000-4000 [nt], A (%) | 9 | 15 | 13 | 23 | 15 | 16 | 10 | 18 | 9 | 17 |
| Ratio of more than 4000 [nt], B (%) | 29 | 38 | 38 | 34 | 41 | 30 | 36 | 31 | 19 | 20 |
| B/A | 3.22 | 2.53 | 2.92 | 1.48 | 2.73 | 1.88 | 3.60 | 1.72 | 2.11 | 1.18 |
| Amplification factor | 0.4 | 1.3 | 1.3 | 1.7 | 1.3 | 1.7 | 1.9 | 0.6 | 1.0 | 2.0 |

(d)

| Tissue | Human gastric tissue FFPE | | | |
|---|---|---|---|---|
| | (29) | (30) | (31) | (32) |
| Purity (OD260/OD280) | 1.87 | 1.92 | 1.95 | 1.92 |
| Ratio of 1000-4000 [nt], A (%) | 8 | 10 | 17 | 26 |
| Ratio of more than 4000 [nt], B (%) | 32 | 30 | 34 | 29 |
| B/A | 4.00 | 3.00 | 2.00 | 1.12 |
| Amplification factor | 1.9 | 1.9 | 1.6 | 1.8 |

Example 2

Extraction of RNA from FFPE

Blocks of formalin-fixed paraffin-embedded (FFPE) cerebellum and liver, which were prepared from mice (7 weeks old, male, Slc:ICR) under various conditions and stored for various periods of time, were prepared as shown in Table 5. From each FFPE block, 10 thin sections having a thickness of 10 μm were collected using a microtome, and placed in 1.5-mL tubes such that 5 thin sections were contained in each tube. To each tube, 1 mL of xylene was added, and the resulting mixture was stirred with a vortex mixer for 10 seconds to dissolve paraffin. After centrifugation at 16,000×g for 5 minutes, xylene was removed using a pipette such that the tissue was not sucked. Subsequently, 1 mL of ethanol was added to the tube, and the resulting mixture was stirred with a vortex mixer for 10 seconds, followed by centrifuging the mixture at 16,000×g for 2 minutes and carefully removing ethanol using a pipette such that the tissue was not sucked. This operation was repeated. The tube was dried in the air with its lid open for 10 minutes, to remove ethanol contained in the tissue. After addition of 100 μL of a proteinase K solution (500 μg/mL), the tissue was suspended, and then left to stand at 37° C. for 16 hours. The tube was centrifuged at 16,000×g for 2 minutes to precipitate and remove the residue, and RNA was then purified using a silica column. The results of measurement of the yield and the purity (ratio between 260 nm and 280 nm) using a spectrophotometer (Thermo Scientific, "Nano Drop" (registered trademark)); the results of calculation of the weight ratio (%) of RNA within the range of 1000 to 4000 nucleotides, A, and the weight ratio (%) of RNA within the range of more than 4000 nucleotides, B, which calculation was carried out with Bioanalyzer; and the values of B/A; are shown in each of Table 4(a) and 4(b).

Amplification of RNA

From 1 μg each of the RNA samples, aminoallyl-modified aRNA (AA-aRNA) was amplified in the same manner as in Example 1. At this time, RNAs extracted from frozen tissues of cerebellum and liver of mice were also amplified in the same manner. The amplification factors calculated based on the yields after the amplification are shown in Table 4. In contrast to the B/A≤1 samples all of which showed amplification factors of not less than 2, the B/A>1 samples showed amplification factors of less than 2.

Fluorescent Labeling and Fragmentation

The above-described aRNAs obtained with amplification factors of not less than 2 were subjected to fluorescent labeling and fragmentation in the same manner as in Example 1. The yields of the aRNAs after the labeling and purification are shown in Table 4.

Micro array Analysis

A solution containing 1000 ng of each RNA was prepared to a final volume of 16 μL with nuclease-free water, and 2 μL of "Hybridization Buffer A" in "3D-Gene (registered trademark) Hybridization Buffer" (Toray Industries, Inc.) was added thereto, followed by subjecting the resulting mixture to heat treatment at 95° C. for 5 minutes. The mixture was rapidly cooled on crushed ice for 3 minutes, and 232 μL of "Hybridization Buffer B plus" was added thereto, followed by stirring the resulting mixture by gentle pipetting, thereby preparing 250 μL of a sample solution. The sample solution was degassed under reduced pressure, and 210 μL of the solution was applied to "3D-Gene (registered trademark) entire mouse genomic DNA chip" (Toray Industries, Inc.). The holes at 4 positions on the cover were closed by sealing, and the chip was placed in a hybridization chamber (Takara Bio Inc., TX711) immobilized on the top panel of Bioshaker (Tokyo Rikakikai, MMS-210). The temperature in the chamber was set to 37° C., and the sample was stirred with swiveling rotation at 250 rpm, to allow the reaction to proceed for 16 hours.

Measurement of Fluorescence Signal Values

After the reaction, the cover of the analysis chip was detached, and the substrate was washed and dried. The substrate was placed in a scanner (Axon Instruments, GenePix (registered trademark) 4000B) for DNA chips, and the signal value (fluorescence intensity) of each fluorescently labeled RNA subjected to the hybridization reaction and the background noise were measured under the conditions of: laser output, 33%; and photomultiplier voltage setting, 500. Among all the spots, 1750 spots were provided as negative control spots for measurement of the background fluorescence value and, from each signal value, the background signal value was subtracted, to calculate the true signal value for each spot. In the case where a spot showed a positive signal value, the spot was regarded as an "effective spot". As a result, as shown in Table 4(a) and 4(b), the number of effective spots was almost equivalent among the samples.

TABLE 4

(a)

| Tissue | Mouse cerebellum FFPE | | | | | |
|---|---|---|---|---|---|---|
| | ① | ② | ③ | ④ | ⑤ | ⑥ |
| Thickness and number of sections used | 10 μm, 5 sections | 10 μm, 5 sections | 10 μm, 10 sections | 10 μm, 5 sections | 10 μm, 5 sections | 10 μm, 5 sections |
| Yield after extraction (μg) | 2.0 | 2.2 | 3.0 | 2.1 | 1.8 | 2.0 |
| Purity (OD260/OD280) | 2.05 | 2.06 | 2.05 | 2.07 | 2.10 | 2.07 |
| Ratio of 1000-4000 [nt], A (%) | 39 | 38 | 52 | 3 | 56 | 4 |
| Ratio of more than 4000 [nt], B (%) | 3 | 4 | 3 | 2 | 4 | 2 |
| B/A | 0.08 | 0.11 | 0.06 | 0.67 | 0.07 | 0.50 |
| Amplification factor | 7.2 | 6.4 | 10.2 | 2.1 | 11.1 | 2.0 |
| Yield after labeling (μg) | 4.3 | 3.7 | 6.3 | 0.8 | 6.5 | 0.6 |
| Number of effective spots | 12200 | 12350 | 12900 | 10430 | 12950 | 10080 |

TABLE 4-continued (b)

| Tissue | Mouse liver FFPE | | | | | |
|---|---|---|---|---|---|---|
| | ① | ② | ③ | ④ | ⑤ | ⑥ |
| Thickness and number of sections used | 10 μm, 2 sections | 10 μm, 2 sections | 10 μm, 5 sections | 10 μm, 5 sections | 10 μm, 5 sections | 10 μm, 5 sections |
| Yield after extraction (μg) | 7.4 | 8.0 | 12.5 | 6.9 | 10.9 | 6.3 |
| Purity (OD260/OD280) | 1.99 | 2.01 | 2.04 | 1.82 | 1.97 | 1.85 |
| Ratio of 1000-4000 [nt], A (%) | 47 | 45 | 64 | 12 | 26 | 14 |
| Ratio of more than 4000 [nt], B (%) | 5 | 6 | 5 | 25 | 16 | 28 |
| B/A | 0.11 | 0.13 | 0.08 | 2.08 | 0.62 | 2.00 |
| Amplification factor | 4.8 | 4.9 | 8.3 | 1.0 | 3.3 | 1.2 |
| Yield after labeling (μg) | 2.9 | 3.1 | 4.8 | — | 1.8 | — |
| Number of effective spots | 12460 | 12300 | 13000 | — | 12100 | — |

Reference Example 2

Figure 2:
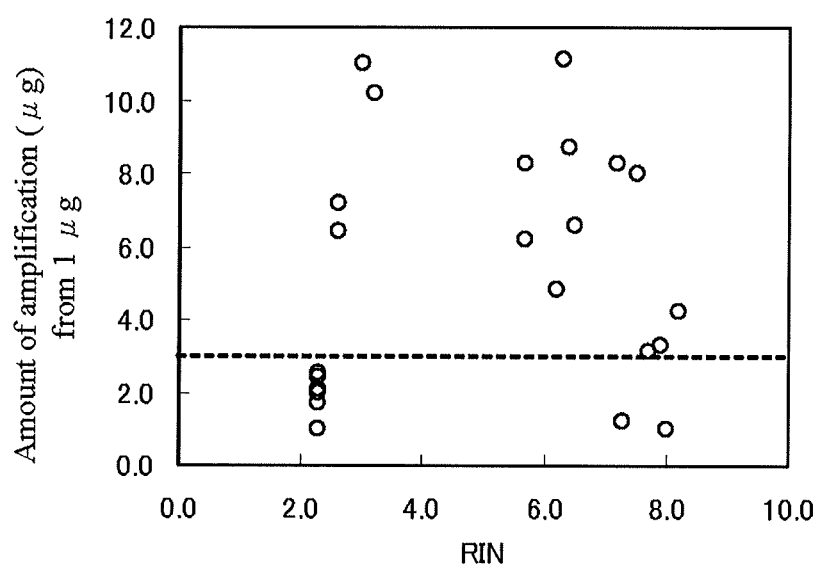
FIG. 2 shows a diagram wherein RINs and the amounts of amplification of various RNAs were plotted.

RNA extracted from FFPE of each of mouse cerebellum, liver and kidney and rat cerebellum and liver in the same manner as in Example 1 was subjected to electrophoresis with Bioanalyzer to calculate RIN. The relationship between the RIN and the yield after amplification with 1 μg of each RNA sample is summarized in FIG. 2 and Table 5(a) to 5(c). As a result, no correlation was found between the RIN and the yield. Further, RIN could not be calculated for a part of the samples (represented as "N/A" in Table 5). Thus, it was shown that, in the case of RNA extracted from a fixed tissue or fixed cell(s) such as FFPE, it is difficult to judge based on RIN whether the sample is suitable for analysis of RNA.

TABLE 5

(a)

| Tissue | Mouse cerebellum FFPE | | | | | | | | | |
|---|---|---|---|---|---|---|---|---|---|---|
| | ① | ② | ③ | ④ | ⑤ | ⑥ | ⑦ | ⑧ | ⑨ | ⑩ |
| RIN | 2.6 | 2.6 | 3.2 | 2.3 | 6.3 | 2.3 | 3.0 | 6.5 | 5.7 | 6.4 |
| Yield after amplification (μg) | 2.0 | 2.2 | 3.0 | 2.1 | 1.8 | 2.0 | 5.8 | 6.3 | 6.7 | 1.9 |

(b)

| Tissue | Mouse liver FFPE | | | | | | | | Mouse kidney FFPE | |
|---|---|---|---|---|---|---|---|---|---|---|
| | ① | ② | ③ | ④ | ⑤ | ⑥ | ⑦ | ⑧ | ① | ② |
| RIN | N/A | N/A | 7.2 | 8.0 | 6.2 | 7.3 | 7.5 | N/A | 7.7 | 7.9 |
| Yield after amplification (μg) | 7.4 | 8.0 | 12.5 | 6.9 | 10.9 | 6.3 | 15.2 | 10.8 | 3.8 | 6.1 |

(c)

| Tissue | Rat cerebellum FFPE | | | | Rat liver FFPE | | | | | |
|---|---|---|---|---|---|---|---|---|---|---|
| | ① | ② | ③ | ④ | ① | ② | ③ | ④ | ⑤ | ⑥ |
| RIN | N/A | 2.3 | 2.3 | 2.3 | 5.7 | 8.2 | N/A | N/A | 2.3 | N/A |
| Yield after amplification (μg) | 2.1 | 1.0 | 2.4 | 2.5 | 8.3 | 4.2 | 2.0 | 0.3 | 1.7 | 1.2 |

Example 3

Extraction of RNA from Fixed Tissue

Blocks of formalin-fixed paraffin-embedded (FFPE) liver, which were prepared from mice (7 weeks old, male, Slc:ICR) with 10% neutral buffered formalin under various conditions and stored for various periods of time, were provided as shown in Table 6 (Samples (A) to (D)). From each block, 2 thin sections having a thickness of 10 μm were collected using a microtome, and the sections were placed in a 1.5-mL tube. To the tube, 1 mL of xylene was added, and the resulting mixture was stirred to dissolve paraffin. After centrifugation at 16,000×g for 5 minutes, xylene was removed using a pipette such that the tissue was not sucked. Subsequently, 1 mL of ethanol was added, and the resulting mixture was stirred, followed by centrifuging the mixture at 16,000×g for 2 minutes and carefully removing ethanol using a pipette such that the tissue was not sucked. This operation was carried out twice. The tube was dried in the air with its lid open for 10 minutes, to remove ethanol contained in the tissue. After addition of 100 μL of a proteinase K solution (500 μg/mL), the tissue was suspended, and then left to stand at 37° C. for 16 hours. The tube was centrifuged at 16,000×g for 2 minutes to remove the residue, and RNA was then purified using a silica column. The results of measurement of the yield and the purity of RNA (ratio between 260 nm and 280 nm) using a spectrophotometer (Thermo Scientific, "Nano Drop" (registered trademark)); the results of calculation of the weight ratio (%) of RNA within the range of 1000 to 4000 nucleotides, A, and the weight ratio (%) of RNA within the range of more than 4000 nucleotides, B, which calculation was carried out with Bioanalyzer; and the values of B/A and A+B; are shown in Table 7. As a control, RNA extracted from a freshly frozen tissue of liver of a mouse (7 weeks old, male, Slc:ICR) was used.

Fluorescent Labeling of RNA

From mouse liver FFPE which is the same as in Example 1, RNA was extracted by the same method, and 500 ng of each extracted RNA was subjected to CIP treatment and then to enzyme reaction for labeling with the Hy5 dye, using "miR-CURY LNA microRNA Array Power Labeling kit" (EX-IQON) according to the protocols attached to the kit.

Microarray Analysis

A solution containing 500 ng of each labeled RNA was prepared to a final volume of 15.4 μL with nuclease-free water, and 0.6 μL of Block Reagent in "3D-Gene (registered trademark) miRNA Hybridization Buffer" (Toray Industries, Inc.) and 105 μL of miRNA Hybridization Buffer were added thereto, followed by mixing the resulting mixture. The mixture was then degassed under reduced pressure, and 110 μL of the mixture was applied to "3D-Gene (registered trademark) Mouse miRNA Chip" (Toray Industries, Inc.). The holes at 4 positions on the cover were closed by sealing, and the chip was placed in a hybridization chamber (Takara Bio Inc., TX711) immobilized on the top panel of Bioshaker (Tokyo Rikakikai, MMS-210). The temperature in the chamber was set to 32° C., and the sample was stirred with swiveling rotation at 250 rpm, to allow the reaction to proceed for 16 hours.

After the reaction, the cover of the chip was detached, and the substrate was washed and dried. The substrate was placed in a scanner (Axon Instruments, GenePix (registered trademark) 4000B) for DNA chips, and the signal value (fluorescence intensity) of each fluorescently labeled RNA subjected to the hybridization reaction and the background noise were measured under the conditions of: laser output, 33%; and photomultiplier voltage setting, 500. Among all the spots, 24 spots were provided as negative control spots for measurement of the background (BG) signal value, and, from each signal value, the BG signal value was subtracted, to calculate the true signal value for each spot. In the case where a spot showed a positive signal value, the spot was regarded as an "effective spot." As a result, as shown in Table 7, the number of effective spots was almost equivalent or rather higher in the samples satisfying B/A≤1, when compared to the control. On the other hand, the number of effective spots was smaller in the samples satisfying B/A>1 than in the control, and it was therefore suggested that there were undetectable miRNAs. Thus, it was shown that whether or not the analysis is possible can be judged based on the value of B/A.

Comparison with Data from RNA Extracted from Frozen Tissue

Further, RNA extracted from a frozen sample of the same tissue was subjected to the same experiment, and the correlation coefficient was calculated for effective spots shared with each FFPE sample-derived RNA. The results are shown in Table 7. In the cases of B/A≤1, high positive correlation with the frozen tissue-derived RNA was found. Further, in Sample (C), wherein B/A≤1 was satisfied and A was not less than 25%, correlation with the freshly frozen sample of the same tissue was not less than 0.9, suggesting a very high correlation. Thus, it was shown that whether or not the analysis is possible can be judged in advance based on the value of B/A.

TABLE 6

| Sample | (A) | (B) | (C) | (D) |
|---|---|---|---|---|
| Period of fixation (Days) | 2 | 2 | 2 | 14 |
| Storage temperature | Room temperature (20 to 25° C.) | Room temperature (20 to 25° C.) | Room temperature (20 to 25° C.) | Refrigeration (4° C.) |
| Period of storage (Months) | 36 | 12 | 6 | 3 |

TABLE 7

| Sample | (A) | (B) | (C) | (D) | Frozen tissue |
|---|---|---|---|---|---|
| Purity (OD260/OD280) | 1.95 | 1.97 | 1.94 | 2.02 | 2.01 |
| Ratio of 1000-4000 [nt], A (%) | 2 | 16 | 39 | 28 | 90 |
| Ratio of more than 4000 [nt], B (%) | 1 | 1 | 4 | 52 | 2 |
| B/A | 0.50 | 0.06 | 0.10 | 1.86 | 0.02 |
| A + B | 3 | 17 | 43 | 80 | 92 |
| Number of effective spots | 344 | 295 | 277 | 203 | 257 |
| Number of effective spots shared with frozen tissue-derived RNA | 202 | 197 | 179 | 120 | — |
| Correlation coefficient with frozen tissue-derived RNA | 0.81 | 0.85 | 0.95 | 0.64 | — |

Example 4

Preparation of Microarray

Using the LIGA (Lithographie Galvanoformung Abformung) process, which is a known method, a mold for injection molding was prepared, and a PMMA substrate having a shape as described below was obtained by injection molding. The average molecular weight of PMMA used in the present Example was 50,000, and carbon black (Mitsubishi Chemical Corporation, #3050B) was included in PMMA with a ratio of 1% by weight to make the substrate black. The spectral reflectance and the spectral transmittance of this black substrate were measured and, as a result, the spectral reflectance was not more than 5% at any wavelength within the visible region (wavelength between 400 nm and 800 nm), and the spectral transmittance was not more than 0.5% within the same range of wavelengths. Neither the spectral reflectance nor the spectral transmittance showed a particular spectral pattern (e.g., peak), and the spectra were uniformly flat. The spectral reflectance was measured with specular reflection from the substrate using a device (Minolta Camera, CM-2002) having an illumination/light-receiving optical system satisfying the condition C of JIS Z 8722.

As the substrate, a polymethylmethacrylate (PMMA) resin substrate (hereinafter referred to as "substrate A") having external dimensions of a longitudinal length of 76 mm, lateral length of 26 mm and thickness of 1 mm was used, which substrate has a recessed portion having a longitudinal length of 39.4 mm, lateral length of 19.0 mm and depth of 0.15 mm at the center, which recessed portion has protruded portions each having a diameter of 0.1 mm and height of 0.15 mm at 9248 positions therein. In this substrate A, the difference in the height between the upper surfaces of the protruded portions and the upper surface of the flat area (the average value, in terms of the protruded portions) was not more than 3 µm. Variation in the height of the upper surfaces of the protruded portions (difference between the height of the upper surface of the highest protruded portion and the height of the upper surface of the lowest protruded portion) was not more than 3 µm. The pitch of the protruded portions (distance between the center of a protruded portion and the center of a protruded portion adjacent thereto) was set to 0.5 mm.

The above substrate A was immersed in 10 N aqueous sodium hydroxide solution at a temperature of 70° C. for 12 hours. The substrate A was then washed sequentially with pure water, 0.1 N aqueous HCl solution and pure water, to allow carboxyl groups to be produced on the surface of the substrate.

To the thus prepared substrate A, sense-strand oligonucleotides were immobilized as selective binding substances (probe DNAs). As the oligonucleotides, an oligonucleotide set for DNA microarrays "*Homo sapiens* (Human) AROS V4.0 (60 bases each)," manufactured by Operon Biotechnologies was used. These oligonucleotides were dissolved in pure water to a concentration of 0.3 nmol/µL, to provide stock solutions. When the stock solutions were to be spotted on the substrate, the stock solutions were 10-fold diluted with PBS (prepared by combining 8 g of NaCl, 2.9 g of $Na_2HPO_4 \cdot 12H_2O$, 0.2 g of KCl and 0.2 g of $KH_2PO_4$, dissolving thereof in pure water to attain a final volume of 1 L, and then adjusting the pH of the resulting solution to 5.5 by addition of hydrochloric acid) to attain a final probe DNA concentration of 0.03 nmol/µL and, to allow condensation between the carboxyl groups produced on the surface of the PMMA substrate and the terminal amino groups of the probe DNAs, 1-ethyl-3-(3-dimethylaminopropyl)carbodiimide (EDC) was added to a final concentration of 50 mg/mL. The resulting solutions were spotted on the upper surfaces of all the protruded portions of the substrate A using an arrayer (spotter) (Nippon Laser & Electronics Lab, Gene Stamp-II). Subsequently, the substrate on which the solution was spotted was placed in a sealed plastic container, and incubated at a temperature of 37° C. and a humidity of 100% for about 20 hours. Finally, the substrate was washed with pure water and dried by centrifugation using a spin drier.

A cover was attached as follows to the substrate A on which the selective binding substances were immobilized. A PMMA flat plate with dimensions of a longitudinal length of 41.4 mm, lateral length of 21 mm and thickness of 1 mm was prepared by cutting and used as the cover. Penetrating holes and liquid level-halting chambers were provided in the prepared cover. The diameter of each penetrating hole was 0.8 mm, and the diameter of each liquid level-halting chamber was 2.0 mm. These were placed at the four corners of the cover. A double-stick tape having a longitudinal length of 41.4 mm, lateral length of 21 mm, width of 1 mm and thickness of 25 µm was cut into a size with which the tape can be placed along the margin of the cover, and the tape was then laminated at a thickness (clearance) of 50 µm and attached to the cover. Thereafter, the cover was attached to the substrate A.

In the substrate A to which the cover was attached as described above, 120 mg of zirconia microparticles having a diameter of 180 µm were encapsulated into the void formed by the substrate A and the cover (the recessed portion of the irregular structure on the surface of the substrate A). The encapsulation of the microparticles was carried out through the penetrating holes on the cover. The thus obtained analysis chip was used in the following study.

Extraction of RNA from Fixed Tissue

In the same manner as in Example 3, thin sections were prepared from blocks of formalin-fixed paraffin-embedded (FFPE) liver which were prepared from mice (7 weeks old, male, Slc:ICR) under various conditions and stored for various periods of time, and RNA was extracted from the thin sections. The results of measurement of the yield and the purity (ratio between 260 nm and 280 nm) using a spectrophotometer (Thermo Scientific, "Nano Drop" (registered trademark)); the results of calculation of the weight ratio (%) of RNA within the range of 1000 to 4000 nucleotides, A, and the weight ratio (%) of RNA within the range of more than 4000 nucleotides, B, which calculation was carried out with Bioanalyzer; and the values of B/A and A+B; are shown in Table 8. As a control, RNA extracted from a freshly frozen tissue of liver of a mouse (7 weeks old, male, Slc:ICR) was used.

Fluorescent Labeling of RNA

The RNA extracted in the same manner as in Example 3 was fluorescently labeled using "PlatinumBright (registered trademark) Nucleic Acid Labeling Kit" (KREATECH). To 1 µg of each RNA, nuclease-free water was added to a final volume of 16 µL, and 2 µL each of ULS reagent and 10× labeling solution were added thereto, followed by allowing the reaction to proceed at 85° C. for 30 minutes, to label mRNA with PlatinumBright 647 dye. "KREApure columns" attached to the kit was used to remove unreacted dye.

Microarray Analysis mRNA contained in each fixed tissue was analyzed by the following procedure. To a solution containing 1 µg of each labeled RNA, nuclease-free water was added to a final volume of 16 µL, and 2 µL of Hybridization Buffer A and 232 µL of Hybridization Buffer B in "3D-Gene (registered trademark) Hybridization Buffer" (Toray Industries, Inc.) were added thereto, followed by mixing the resulting mixture and degassing the mixture under reduced pressure. To the above-prepared analysis chip, 210 µL of the mixture was applied. The holes at the 4 positions on the cover were closed by sealing, and the chip was placed in a hybridization chamber (Takara Bio Inc., TX711) immobilized on the top panel of Bioshaker (Tokyo Rikakikai, MMS-210). The temperature in the chamber was set to 37° C., and the samples were stirred with swiveling rotation at 250 rpm, to allow the reaction to proceed for 16 hours.

Measurement of Fluorescence Signal Values

After the reaction, the cover of the analysis chip was detached, and the substrate was washed and dried. The substrate was placed in a scanner (Axon Instruments, GenePix (registered trademark) 4000B) for DNA chips, and the signal value (fluorescence intensity) of each fluorescently labeled RNA subjected to the hybridization reaction and the background noise were measured under the conditions of: laser output, 33%; and photomultiplier voltage setting, 500. Among all the spots, 32 spots were provided as negative control spots for measurement of the background fluorescence value, and, from each signal value, the background signal value was subtracted, to calculate the true signal value for each spot. In the case where a spot showed a positive signal value, the spot was regarded as an "effective spot". As a result, as shown in Table 8, the numbers of effective spots in the samples satisfying B/A≤1 were not largely different from that in reference RNA extracted from a freshly frozen mouse liver tissue, and it was confirmed that there tends to be a high correlation in terms of shared effective spots. Further, the larger the value A, the more remarkable the tendency. On the other hand, the number of effective spots in the sample satisfying B/A>1 was smaller than in the reference RNA, and it was therefore suggested that undetectable mRNAs exist in the sample.

Comparison with Data from RNA Extracted from Frozen Tissue

Further, RNA extracted from a frozen sample of the same tissue was subjected to the same experiment, and the correlation coefficient was calculated for effective mRNA spots shared with each FFPE specimen-derived RNA. The correlation coefficient for each sample was as shown in Table 8 and, in the cases where B/A≤1 was satisfied, high correlations with the frozen tissue-derived RNA could be confirmed. Further, it was shown that the sample (C), wherein B/A≤1 was satisfied and A was not less than 25%, has a correlation of not less than 0.9 with the freshly frozen sample of the same tissue, indicating a very high correlation. Therefore, it was shown that whether or not the analysis is possible can be judged based on the value of B/A.

TABLE 8

| Sample | (A) | (B) | (C) | (D) | Frozen tissue |
|---|---|---|---|---|---|
| Purity (OD260/OD280) | 1.95 | 1.97 | 1.94 | 2.02 | 2.01 |
| Ratio of 1000-4000 [nt], A (%) | 2 | 16 | 39 | 28 | 90 |
| Ratio of more than 4000 [nt], B (%) | 1 | 1 | 4 | 52 | 2 |
| B/A | 0.50 | 0.06 | 0.10 | 1.86 | 0.02 |
| A + B | 3 | 17 | 43 | 80 | 92 |
| Number of effective spots | 19877 | 17960 | 16121 | 11836 | 15782 |
| Number of effective spots shared with frozen tissue-derived RNA | 14012 | 13749 | 13998 | 7298 | — |
| Correlation coefficient with frozen tissue-derived RNA | 0.72 | 0.80 | 0.91 | 0.53 | — |

TABLE 9

| | Mouse cerebellum | | Mouse liver | |
|---|---|---|---|---|
| Tissue | FFPE | Frozen | FFPE | Frozen |
| Thickness and number of sections used | 10 μl, 10 sections | — | 10 μm, 2 sections | — |
| Yield after extraction (μg) | 3.8 | — | 10.1 | — |

TABLE 9-continued

| | Mouse cerebellum | | Mouse liver | |
|---|---|---|---|---|
| Tissue | FFPE | Frozen | FFPE | Frozen |
| Purity (OD260/OD280) | 1.98 | 2.08 | 1.99 | 2.07 |
| Ratio of 1000-4000 [nt], A (%) | 27 | 89 | 28 | 87 |
| Ratio of more than 4000 [nt], B (%) | 16 | 2 | 19 | 3 |
| B/A | 0.59 | 0.02 | 0.68 | 0.03 |
| Amplification factor | 4.2 | 19.0 | 3.1 | 16.9 |
| Number of detected genes | 9870 | 14985 | 9584 | 14391 |
| Correlation coefficient | 0.88 | | 0.85 | |

Example 5

From each of FFPE samples of mouse cerebellum and liver, sections having a thickness of 10 μm were prepared, and RNA was extracted therefrom by the same method as in Example 1. In the same manner as in Example 2, amplification reaction was carried out for 1 μg of the RNA as well as RNA extracted from freshly frozen tissues of mouse cerebellum and liver, to obtain aRNA. The yield and the purity of RNA; the weight ratio (%) of RNA within the range of 1000 to 4000 nucleotides, A, and the weight ratio (%) of RNA within the range of more than 4000 nucleotides, B, as measured by Bioanalyzer; and the amplification factor are shown in Table 9. The aRNA was labeled with Cy3 (GE Healthcare) and mixed with the hybridization buffer in "Gene Expression Hybridization Kit" (Agilent Technologies), followed by hybridization on "Whole Mouse Genome Oligo Microarray (4×44 k)" (Agilent Technologies) for 40 hours. After washing the microarray, an image of the DNA microarray was read by "Agilent Microarray Scanner" (Agilent Technologies), and the fluorescence signal from each spot was digitized with "Feature Extraction Software (v.9.5.3.1)." As a result, as shown in Table 9, the correlation coefficients were shown to be as high as 0.88 for cerebellum and 0.85 for liver.

Example 6

Using the mouse cerebellum and liver FFPE-derived RNAs and the frozen tissue-derived RNAs extracted in Example 5, amplification reaction was performed with 5 μg of each RNA in the same manner as in Example 1, to obtain aRNA. At this time, biotin groups were introduced instead of aminoallyl groups. The amplification factors were as shown in Table 10. The biotinylated aRNA was mixed with a predetermined amount of Control Oligonucleotide, 20× Eukaryotic Hybridization Controls, 2× Hybridization Mix, DMSO and nuclease-free water, followed by treating the resulting mixture at 99° C. for 5 minutes and then at 45° C. for 5 minutes. Further, the mixture was centrifuged at 16,000×g for 5 minutes and applied to "Affymetrix (registered trademark) Mouse Genome 430 2.0 Array" (Affymetrix, Inc.), followed by allowing hybridization reaction to proceed for 16 hours. After washing and staining of the array by predetermined methods, the fluorescence signal from each spot was digitized with "GeneChip (registered trademark) Scanner 3000 7G System" (Affymetrix, Inc.). As a result, as shown in Table 10, although the number of effective spots in FFPE tended to be smaller relative to the frozen tissues, the correlation coefficients between these were 0.84 for cerebellum and 0.82 for liver, so that a high correlation could be confirmed.

TABLE 10

| | Mouse cerebellum | | Mouse liver | |
|---|---|---|---|---|
| Tissue | FFPE | Frozen | FFPE | Frozen |
| Amplification factor | 4.1 | 17.3 | 3.0 | 15.5 |
| Number of detected genes | 8248 | 12961 | 8060 | 12408 |
| Correlation coefficient | 0.84 | | 0.82 | |

Example 7

Extraction of RNA from Fixed Tissues

Cerebellum and liver were removed from mice (7 weeks old, male, Slc:ICR) and immersed in 10% phosphate-buffered formalin solution (4% formaldehyde) for 2 days at room temperature for fixation, followed by paraffin embedding to prepare FFPE blocks. From each FFPE block, thin sections having a thickness of 10 μm were collected using a microtome, and RNA was extracted in the same manner as in Example 1. The results of measurement of the yield and the purity (ratio between 260 nm and 280 nm) using a spectrophotometer (Thermo Scientific, "Nano Drop" (registered trademark)); the results of calculation of the weight ratio (%) of RNA within the range of 1000 to 4000 nucleotides, A, and the weight ratio (%) of RNA within the range of more than 4000 nucleotides, B, which calculation was carried out with Bioanalyzer; and the value of B/A; are shown in Table 11. All the samples satisfied B/A≤1.

Amplification of RNA

With 1 μg each of the RNAs extracted from mouse cerebellum and liver, amplification was carried out in the same manner as in Example 1 to obtain aRNA to which aminoallyl groups were introduced. The yield was determined with a spectrophotometer (Thermo Scientific, "Nano Drop" (registered trademark)) to calculate the amplification factor, and the results are shown in Table 11. All the samples showed an amplification factor within the range of 2 to 20.

Fluorescent Labeling, Fragmentation and Microarray Analysis of Amplified RNA

Each amplified aRNA was subjected to fluorescent labeling and fragmentation in the same manner as in Example 1, and microarray analysis was carried out by the following operation. A solution containing 1000 ng of each RNA was prepared to a final volume of 16 μL with nuclease-free water, and 2 μL of "Hybridization Buffer A" in "3D-Gene" (registered trademark) Hybridization Buffer (Toray Industries, Inc.) was added thereto, followed by subjecting the resulting mixture to heat treatment at 95° C. for 5 minutes. The mixture was rapidly cooled on crushed ice for 3 minutes, and 232 μL of "Hybridization Buffer B" was added thereto, followed by stirring the resulting mixture by gentle pipetting, thereby preparing 250 μL of a sample solution. The sample solution was degassed under reduced pressure, and 210 μL of the solution was applied to "3D-Gene (registered trademark) entire mouse genomic DNA chip" (Toray Industries, Inc.). The holes at 4 positions on the cover were closed by sealing, and the chip was placed in a hybridization chamber (Takara Bio Inc., TX711) immobilized on the top panel of Bioshaker (Tokyo Rikakikai, MMS-210). The temperature in the chamber was set to 37° C., and the sample was stirred with swiveling rotation at 250 rpm, to allow the reaction to proceed for 16 hours.

Measurement of Fluorescence Signal Values

Figure 3:
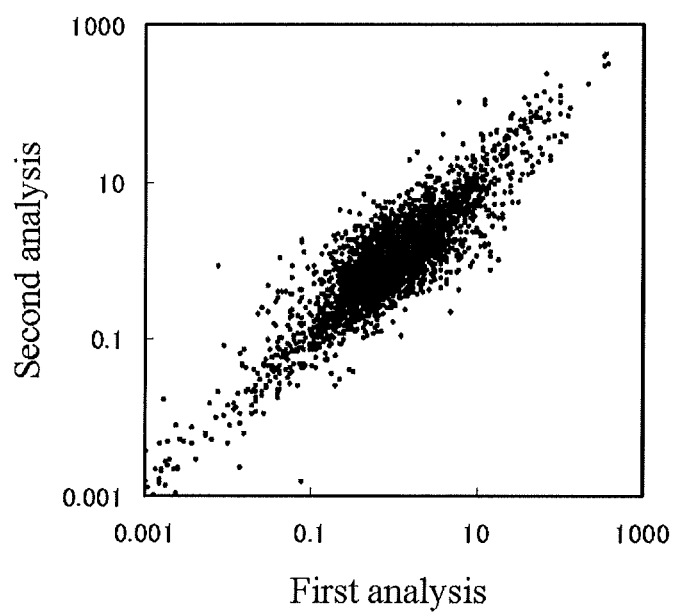
FIG. 3 shows a scatter diagram prepared by performing expression analysis twice for mouse cerebellum and liver FFPE tissues using a microarray, thereby measuring the signal intensity for each gene in each of the first and second analyses, followed by plotting the cerebellum/liver ratios determined from these analyses.

After the reaction, the cover of the analysis chip was detached, and the substrate was washed and dried. The substrate was placed in a scanner (Axon Instruments, "GenePix (registered trademark) 4000B") for DNA chips, and the signal value (fluorescence intensity) of each fluorescently labeled RNA subjected to the hybridization reaction and the background noise were measured under the conditions of: laser output, 33%; and photomultiplier voltage setting, 500. Among all the spots, 1750 spots were provided as negative control spots for measurement of the background fluorescence value, and, from each signal value, the background signal value was subtracted, to calculate the true signal value for each spot. In the case where a spot showed a positive signal value, the spot was regarded as an "effective spot." The numbers of effective spots are shown in Table 11. It was shown that the variation in the number of effective spots is small within the same tissue. A scatter diagram prepared based on the signal ratios for the respective genes between cerebellum and liver (cerebellum/liver) is shown in FIG. 3. From this result, it was shown that the results obtained by the two times of experiments are highly correlated with each other.

TABLE 11

| Tissue | Mouse cerebellum FFPE | | Mouse liver FFPE | |
| --- | --- | --- | --- | --- |
| | ① | ② | ① | ② |
| Thickness and number of sections used | 10 μl, 5 sections | 10 μl, 5 sections | 10 μl, 2 sections | 10 μl, 2 sections |
| Yield after extraction (μg) | 2.0 | 2.2 | 7.4 | 8.0 |
| Purity (OD260/OD280) | 2.05 | 2.06 | 1.99 | 2.01 |
| Ratio of 1000-4000 [nt], A (%) | 31 | 29 | 40 | 39 |
| Ratio of more than 4000 [nt], B (%) | 9 | 7 | 15 | 14 |
| B/A | 0.29 | 0.24 | 0.38 | 0.36 |
| Amplification factor | 7.2 | 6.4 | 4.8 | 4.9 |
| Number of effective spots | 12200 | 12350 | 12460 | 12300 |

INDUSTRIAL APPLICABILITY

By using our method for analyzing RNA, accurate information on increase/decrease in expression or the presence/absence of expression of genes in a vast number of fixed tissues and cells such as formalin-fixed paraffin-embedded tissues stored in hospitals and research institutes can be obtained. Such information can be widely used for development of pharmaceuticals, techniques of genetic testing and genetic diagnosis and the like. Further, by preliminarily identifying samples which are difficult to analyze and removing those samples from the subject of analysis, the cost for reagents and the like can be reduced, so that our method is industrially very useful.

The invention claimed is:

1. A method of analyzing microarray analysis of RNA extracted from a fixed tissue or fixed cell(s) fixed with a fixative, said method comprising a) subjecting the RNA to electrophoresis, b) a determining step of whether said RNA satisfies:

$B/A \leq 1$ wherein A represents the weight ratio (%) of RNA within the range of 1000 to 4000 nucleotides with respect to the total weight of RNA as determined by electrophoresis, and B represents the weight ratio (%) of RNA within the range of more than 4000 nucleotides with respect to the total weight of RNA as determined by electrophoresis, and c) carrying out microarray analysis with the RNA if B/A≤1.

2. The method for analyzing RNA according to claim 1, further comprising determining whether said ratio A (%) is not less than 25%.

3. The method for analyzing RNA according to claim 1, wherein an amplification product obtained by amplification of said RNA with an amplification factor of 2 to 20 is analyzed.

4. The method for analyzing RNA according to claim 1, wherein said RNA is analyzed without amplification.

5. The method for analyzing RNA according to claim 4, wherein said RNA is miRNA.

6. The method for analyzing RNA according to claim 1, wherein said fixative comprises formaldehyde and/or paraformaldehyde.

7. The method for analyzing RNA according to claim 1, wherein said tissue or cell(s) fixed with a fixative is/are embedded in paraffin or embedded in OCT compound.

8. A method of analyzing RNA comprising:
extracting the RNA from a fixed tissue or fixed cell(s);
determining whether said RNA satisfies:

$$B/A \leq 1$$

wherein A represents the weight ratio (%) of RNA within the range of 1000 to 4000 nucleotides with respect to the total weight of RNA as determined by electrophoresis, and B represents the weight ratio (%) of RNA within the range of more than 4000 nucleotides with respect to the total weight of RNA as determined by electrophoresis, and
carrying out microarray analysis with the RNA if $B/A \leq 1$.

9. A method of analyzing RNA extracted from a fixed tissue or fixed cell(s) fixed with a fixative comprising:
subjecting the RNA to electrophoresis;
measuring weight of RNA comprising 1000 to 4000 nucleotides from the extracted RNA by electrophoresis;
measuring weight of RNA comprising more than 4000 nucleotides from the extracted RNA by electrophoresis;
determining whether the RNA satisfies: $B/A \leq 1$, wherein A represents a weight ratio (%) of the RNA comprising 1000 to 4000 nucleotides with respect to total weight of the extracted RNA, and B represents a weight ratio (%) of the RNA comprising more than 4000 nucleotides with respect to the total weight of the extracted RNA, and
carrying out microarray analysis with the RNA if $B/A \leq 1$.

* * * * *